United States Patent [19]

Potter et al.

[11] Patent Number: 4,659,328
[45] Date of Patent: Apr. 21, 1987

[54] STYLET

[75] Inventors: Lawrence A. Potter, Whitehouse; James Sgro, South Bound Brook, both of N.J.

[73] Assignee: Biosearch Medical Products, Inc., Somerville, N.J.

[21] Appl. No.: 588,503

[22] Filed: Mar. 12, 1984

[51] Int. Cl.[4] ............................................. A61M 25/00
[52] U.S. Cl. ..................... 604/170; 604/164; 128/657; 128/772
[58] Field of Search ................. 604/170, 164, 93, 165; 128/348.1, 657, 772

[56] References Cited

U.S. PATENT DOCUMENTS

| 1,906,678 | 5/1933 | Wappler | 604/170 |
| 1,920,006 | 7/1933 | Dozier | 604/170 |
| 2,118,631 | 5/1938 | Wappler | 604/170 |
| 2,463,149 | 3/1949 | Caine | 128/200.26 |
| 3,528,406 | 9/1970 | Jeckel | 604/170 |
| 3,896,815 | 7/1975 | Fettel et al. | 128/348.1 |
| 4,388,076 | 6/1983 | Waters | 604/165 |
| 4,496,347 | 1/1985 | MacLean et al. | 604/164 |
| 4,545,390 | 10/1985 | Leary | 128/772 |
| 4,548,206 | 10/1985 | Osborne | 128/772 |
| 4,554,929 | 11/1985 | Samson et al. | 128/772 |

FOREIGN PATENT DOCUMENTS 0969892 12/1950 France ...................... 604/264

Primary Examiner—Stephen C. Pellegrino
Assistant Examiner—Gene B. Kartchner
Attorney, Agent, or Firm—Hoffmann, Dilworth, Barrese & Baron

[57] ABSTRACT

A stylet 2 for stiffening a pliable infusion tube 38 comprising a wire 4 extending between a proximal and a distal end, a coiled spring 22 providing a flexible tip to the distal end of the stylet 2 for more easily feeding the stylet 2 through a convoluted infusion tube 38, a reduced diameter portion 26 of the coiled spring 22 telescoped over the distal end 20 of the wire 4 and bonded thereto, an enlarged end 32 of the coiled spring 22 for preventing the wire tip from exiting from the tube 38 through the tube wall or through openings 58, 60 in the tube 38, and a crimped coil 68 in the spring 22 for limiting the position of the distal end of the wire 4 in the spring 22, a connector 40 mounted on the tube proximal end, a bolus 50 mounted on the tube distal end, a connector 10 mounted on the proximal end of the wire 4, spring 22 being adapted to be seated in the bolus 50, wire 4 being longer than tube 38, whereby when proximal end connector 40 of the tube abuts the proximal end connector 10 of the wire 4, the bolus 50 exerts pressure against the spring 22 to compress the spring 22 and insure that it remains firmly seated in the bolus 50.

16 Claims, 3 Drawing Figures

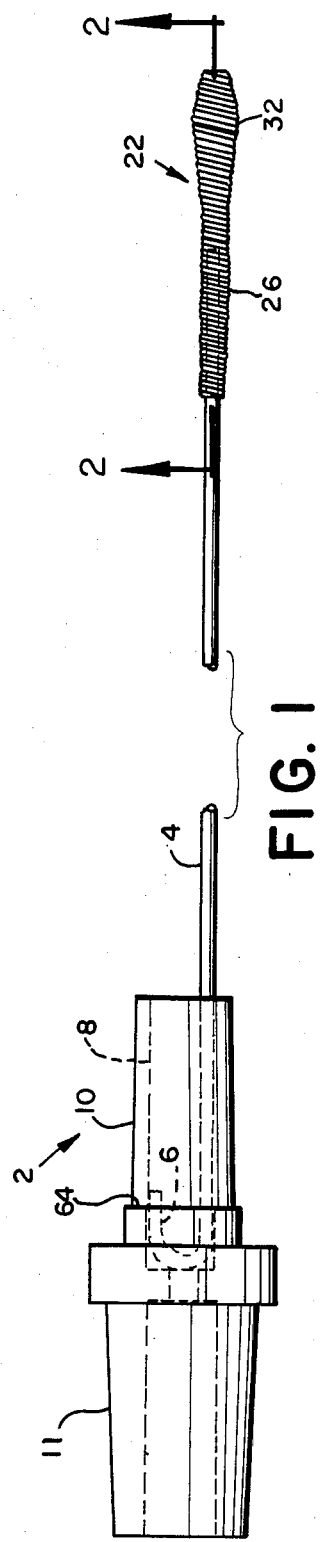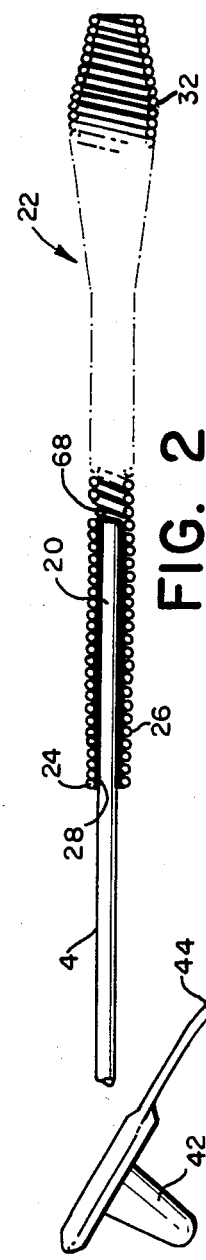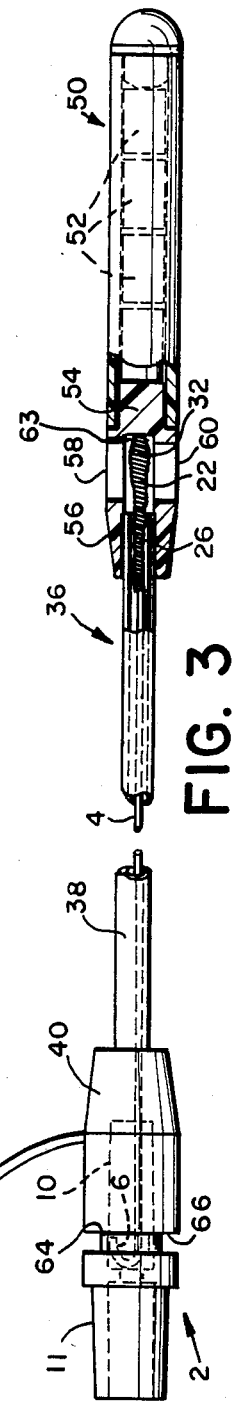

STYLET

TECHNICAL FIELD

This invention is in the field of medical devices.

BACKGROUND OF PRIOR ART

Stylets to stiffen pliable infusion tubes to be inserted into a body as well-known in the prior art as seen for example in U.S. Pat. No. 4,388,076 and in the patents referred to in said patent. Generally, the stylet is inserted into the tube prior to the insertion of the tube into the body. For most applications, the stylet is then withdrawn with the tube remaining properly in place in the body. However, in many cases, it is desired to reinsert the stylet into the tube, e.g. for repositioning. When the tube has convolutions in it, as is always the case with, for example, a NASO-enteric feeding tube, it is difficult to feed the stylet through the tube even when the stylet leading end is provided with an enlarged ball-shaped end as is used in the prior art. Not only is it difficult to reinsert the stylet into the tube under these circumstances, but also the force necessary for the insertion may cause the distal inflexible end of the stylet to puncture the wall of the tube or force it through a distal tube outlet hole.

These problems have been solved by this invention by providing a unique flexible tip on the distal end of the stylet which readily follows the convolutions of the tube lumen into which it is being inserted.

BRIEF SUMMARY OF THE INVENTION

A flexible tip is secured to the distal end of a stylet wire. The flexible tip comprises a tightly coiled helical spring which may be under compression when it is sealed in an enteric feeding tube. Advantageously, the outer end of the spring is enlarged in diameter to prevent the flexible tip from exiting the tube by piercing the tube wall or by passing through a distal tube outlet. Preferably, the spring has an attachment portion that is telescoped over and bonded to the distal end of the stylet wire for better bonding between them and for preventing the end of the wire from breaking free of the spring and presenting a danger of piercing the wall of the tube. A positive stop in the form of a crimp in the spring prevents the wire tip from moving forward into the spring body.

BRIEF DESCRIPTION OF THE DRAWINGS

FIG. 1 is a plan view of the stylet in accordance with the invention, partially broken away.

FIG. 2 is an enlarged plan view of the tip of the stylet of FIG. 1; and

FIG. 3 is a plan view, partially broken away, of the stylet of FIG. 1 inserted into an enteric feeding tube.

DETAILED DESCRIPTION

By way of specific illustration, a stylet suitable for use with an enteric feeding tube will be described.

A stylet 2 in accordance with the invention has a wire 4 with a hook 6 engaging the tapered inside wall 8 of a hollow male plug connection 10 with the end of the hook 6 jabbing into the wall 8. Integral with plug 10 and in fluid communication therewith is a female luer connector 11. As described up to this point, the structure is disclosed in detail in U.S. Pat. No. 4,388,076, incorporated herein by reference, and hence need not be further detailed here.

The distal end 20 of wire 4 has secured thereto a tightly coiled helical spring 22 formed by coiling a spring wire 24 to form spring coil loops having cross sections substantially transverse the linear axis of the coiled helical spring 22. As can be seen from the figures, the gauge of the spring wire 22 can be less, even to a substantial degree, than the gauge of the wire 4. The inner end 26 of spring 22 is telescoped over the distal end 20 of wire 4 and is secured thereto by a low melt solder 28. It will be evident that other means of securing spring 22 to wire 4 may be employed such as, for example, by brazing, silver soldering, or welding. Wire 24 preferably is of stainless steel, for medical reasons because it is easily sterilized, is toxicologically inert, and has a small diameter in the range of from about 0.005 to about 0.015 inches so that the outer diameter of the inner end 26 of spring 22 exceeds the outer diameter of wire 4 by only a small amount. The solder used may be, for example, 5% of silver and 95% of tin.

The outer end 32 of spring 22 has an enlarged diameter to provide for a wider distribution of the forces exerted by coil spring 22 on the wall of a tube through which it is passed so as to inhibit piercing of the tube wall by end 32 of spring 22.

Referring now to FIG. 3, the stylet 2 is shown inserted into an intubating device 36 suitable, for example, for enteric feeding. The device 36 has a flexible tube 38 of any material conventionally used for such tubes such as polyurethane, polyethylene or polyvinyl chloride. A female luer connection 40 is secured to the proximal end of the tube 38 and has a cap plug 42 secured thereto by an integral strap 44.

A hollow tip or bolus 50 often contains weighted material such as mercury or a plurality of weights 52 secured therein and is secured to a plug 54, the inner end 56 of which is telescoped over the distal end of tube 38 and is bonded thereto. Opposed openings 58 and 60 provide for the passage of fluid into tube 38 when feeding and out of tube 38 when aspirating. Openings 58 and 60 are made sufficiently small so that the enlarged outer end 32 of spring 22 cannot pass through them. As seen in FIG. 3, the outer end 32 of spring 22 is seated in a recess 63 in plug 54 which prevents end 32 from moving from side to side.

A shoulder 64 of connection 10 abuts against face 66 of luer connection 40 to accurately limit the movement of wire 4 into tube 38. In order to position shoulder 64 against face 66, it is necessary to stretch tube 38 somewhat which is advantageous in that it forces end 32 of coil spring 22 into recess 63 and keeps it there slightly in compression. As shown in FIG. 3, the stylet 2 is fully inserted, with shoulder 64 interfacing with face 66 of luer connection 40 which causes tube 38 to be stretched.

A positive stop crimp 68 is made in the inner end 26 of spring 22 to prevent the tip of wire 4 from moving forward towards the outer end 32 of the spring 22. If the tip of wire 4 is too far forward in spring 22, the spring loses desired flexibility. If the tip of wire 4 is not far enough forward in spring 22, the spring loses desired stiffness.

We claim:

1. A stylet for stiffening a pliable infusion tube used for selective enteric administration and aspiration of fluids to and from the gastrointestinal tract of a patient, said tube having at least one aperture proximal the distal end thereof, and said stylet capable of being fixed in said tube without interruption of fluid communication through said tube and said aperture comprising:
a wire extending between a proximal end of said tube and said distal end and having a transverse cross-section with an outside perimeter smaller than the inside perimeter of the transverse cross-section of said tube whereby fluid passes between said wire and said tube when in use,
elongated resilient flexible means for providing a flexible tip proximal to the distal end of said stylet, said resilient flexible means comprising a helically coiled spring wire with a linear axis and with spring coils forming loops oriented substantially transversely of said linear axis, said coiled spring wire oriented in the linear direction in the relaxed condition whereby said flexible means returns to the elongated linear condition upon release from severe deformation in any direction, and constructed for passage of fluid therethrough, said flexible means further having two ends, one end having means for presenting said styled from exiting through said aperture and the other end connected to said distal end of said wire, said means for preventing said stylet from exiting said aperture comprising enlarged spring coil loops proximate said one end which have a cross-section dimension greater than said aperture to prevent said flexible means from passing through said aperture, and said enlarged coil loops preceded on said one end by coils of gradually smaller cross-sections whereby a smooth circumferential shoulder is provided for contact with said infusion tube,
connecting means connecting said other end of said resilient means to said distal end of said wire co-linearly with said wire whereby said stylet positioned in said tube stiffens said pliable infusion tube while maintaining fluid communication through said tube and said aperture.

2. The stylet of claim 1 wherein said connecting means comprises coiled spring wire loops having a substantially reduced diameter for telescoping over said distal end of said wire.

3. The stylet of claim 2 wherein said reduced diameter portion of said coiled spring wire is bonded to said distal end of said wire by one of soldering, brazing and welding.

4. The stylet of claim 1 wherein said connecting means further comprises positive stop means fixing the linear extension of said distal end of said wire in said elongated resilient flexible means.

5. The stylet of claim 4 wherein said positive stop means comprises a crimped coil in said spring.

6. The stylet of claim 1 wherein said wire extending between said proximal and said distal end of said tube is a single strand wire.

7. The feeding tube assembly of claim 8 wherein said wire extending between said proximal and said distal end of said tube is a single strand wire.

8. A feeding tube assembly for selective enteric administration and aspiration of fluids to and from the gastrointestinal tract of a patient comprising:
pliable infusion tube which has a proximal end and a distal end having an end wall and at least one aperture in the side wall proximate said end wall,
a first connector mounted on the proximal end of said tube,
a stylet for stiffening said pliable infusion tube with a second connector mounted on the proximal end thereof comprising a wire extending between said proximal end of said tube and said distal end and having a transverse cross-section with an outside perimeter smaller than the inside perimeter of the transverse cross-section of said tube whereby fluid passes between said wire and said tube while in use, elongated locally resilient flexible means for providing a flexible tip to the distal end of said stylet, said resilient flexible means comprising a helically coiled spring wire with a linear axis and with spring coils forming loops oriented substantially transversely of said linear axis, said coiled spring wire oriented in the linear direction in the relaxed condition whereby said flexible means returns to the elongated linear condition upon release from severe deformation in any direction, and constructed for passage of fluid therethrough, said flexible means further having two ends, one end having means for preventing said styled from exiting through said aperture and the other end connected to said distal end of said wire, said means for preventing said stylet from exiting said aperture comprising enlarged spring coil loops at said one end which have a cross-section dimension greater than said aperture whereby said flexible means is prevented from passing through said aperture, and wherein said enlarged coils are preceded on said one end by coils of gradually smaller cross-sections whereby a smooth circumferential shoulder is provided for contact with said infusion tube, and connecting means connecting said other end of said resilient means to said distal end of said wire co-linearly with said wire, said stylet having an overall length slightly longer than said tube whereby said stylet positioned in said tube stiffens said pliable infusion tube while maintaining fluid communication through said tube and said aperture.

9. The feeding tube assembly of claim 8 which further comprises a bolus mounted on said distal end of said tube which includes said end wall of said infusion tube.

10. The feeding tube assembly of claim 8 wherein said second connector includes an opening therethrough for passage of fluid between the interior of said tube and the exterior end of said connector.

11. The feeding tube assembly of claim 8 wherein said connecting means comprises coiled spring wire loops having a substantially reduced-diameter for telescoping over said distal end of said wire.

12. The feeding tube assembly of claim 11 wherein said reduced diameter portion of said coiled spring wire is bonded to said distal end of said wire by one of soldering, brazing and welding.

13. The feeding tube assembly of claim 8 wherein said connecting means further comprises positive stop means fixing the linear extension of said distal end of said wire in said elongated resilient flexible means.

14. The feeding tube assembly of claim 13 wherein said positive stop means comprises a crimped coil in said spring.

15. The stylet of claim 1 wherein said coiled spring wire a lesser gauge than the gauge of said wire extending between said proximal and said distal end of said tube.

16. The feeding tube assembly of claim 8 wherein said coiled spring wire is a lesser gauge than the gauge of said wire extending between said proximal and said distal end of said tube.

* * * * *